United States Patent
Taminiau

(10) Patent No.: US 10,898,734 B2
(45) Date of Patent: Jan. 26, 2021

(54) RADIATION THERAPY APPARATUS

(71) Applicant: Elekta Limited, West Sussex (GB)

(72) Inventor: Danny Taminiau, Crawley (GB)

(73) Assignee: Elekta Limited, Crawley (GB)

( * ) Notice: Subject to any disclaimer, the term of this patent is extended or adjusted under 35 U.S.C. 154(b) by 0 days.

(21) Appl. No.: 16/540,212

(22) Filed: Aug. 14, 2019

(65) Prior Publication Data
US 2020/0054898 A1 Feb. 20, 2020

(30) Foreign Application Priority Data
Aug. 15, 2018 (GB) .................................. 1813314.0

(51) Int. Cl.
*G21K 1/00* (2006.01)
*A61N 5/10* (2006.01)

(52) U.S. Cl.
CPC .... *A61N 5/1081* (2013.01); *A61N 2005/1092* (2013.01)

(58) Field of Classification Search
CPC .......... A61N 5/1081; A61N 2005/1092; A61N 2005/1074; A61N 5/1045; A61N 5/1039; A61N 5/1077
See application file for complete search history.

(56) References Cited

U.S. PATENT DOCUMENTS

| 2013/0006091 A1 | 1/2013 | Manjeshwar et al. |
| 2016/0045769 A1* | 2/2016 | Amelia ................ A61N 5/1042 600/1 |

FOREIGN PATENT DOCUMENTS

| EP | 1958663 A1 | 8/2008 |
| EP | 2119411 A1 | 11/2009 |
| GB | 2519595 A | 4/2015 |
| GB | 2519605 A | 4/2015 |
| WO | WO-03070101 A1 | 8/2003 |
| WO | WO-2005089039 A2 | 9/2005 |
| WO | WO-2006120676 A1 | 11/2006 |
| WO | WO-2018093933 A1 | 5/2018 |

OTHER PUBLICATIONS

"European Application No. 19191206.2, Extended European Search Report dated Jan. 15, 2020", (dated Jan. 15, 2020), 7 pgs.
"United Kingdom Application Serial No. 1813314.0, Search Report dated Sep. 18, 2018", (dated Sep. 18, 2018), 3 pgs.

\* cited by examiner

*Primary Examiner* — Kiho Kim
(74) *Attorney, Agent, or Firm* — Schwegman Lundberg & Woessner, P.A.

(57) ABSTRACT

A moveable support frame for a radiotherapy device, wherein the moveable support frame comprises at least one mass compensation mechanism, wherein the mass compensation mechanism comprises at least one resilient element.

20 Claims, 6 Drawing Sheets

RADIATION THERAPY APPARATUS

CLAIM FOR PRIORITY

This application claims the benefit of priority of United Kingdom Application No. 1813314.0, filed Aug. 15, 2018, which is hereby incorporated by reference in its entirety.

TECHNICAL FIELD

The present disclosure relates to a radiation therapy apparatus. More particularly, the disclosure provides a radiation therapy apparatus that allows for convenient maintenance and repair.

BACKGROUND

Radiation therapy is a localised treatment designed to treat an identified tissue target, such as a cancerous tumour, and spare the surrounding normal tissue from receiving doses above specified tolerances thereby minimising risk of damage to healthy tissue. Prior to delivery of radiation therapy, an imaging system can be used to provide a three-dimensional image of the target from which the target size and mass can be estimated and appropriate treatment plan determined.

Many factors may contribute to differences between the dose distribution determined in the treatment plan and the delivered dose distribution. One such factor is an inconsistency between the patient position at the imaging stage and the patient position in the radiation treatment unit. Image guided radiation therapy (IGRT) involves the use of an imaging system to view target tissues prior to or whilst radiation treatment is being delivered to the target tissue. IGRT incorporates imaging coordinates from the treatment plan to ensure that the patient is properly aligned for treatment in the radiation therapy device.

The applicant's prior published International Patent Application No. PCT/GB02/03339 describes an IGRT, which includes the functions of an MRI device in a radiation therapy treatment apparatus. MRI is ideal for on-line position verification during radiotherapy because it is able to make fast 2D images of soft tissues with orientation along and perpendicular to the field axis, allowing imaging at critical locations, which are defined during the treatment planning procedure. MRI also provides excellent contrast between tissue types giving a sharp image of the target.

The large scale of these combined devices will be appreciated and is described in the applicant's earlier granted UK patents GB2519605 and GB2519595. The device comprises a large ring gantry onto which a linear accelerator (LINAC) is mounted and arranged to travel around targets positioned at the isocentre of the ring. An MRI sits in the aperture of the ring gantry sharing the isocentre. The body to be treated is introduced into a treatment space at the isocentre by means of a sliding table. In order to accommodate the imaging component within the radiation therapy component, the gantry in such devices is typically of the order of two to three metres in diameter and of a considerable weight.

GB2519605 and GB2519595 describe the problems of transporting and manoeuvring such equipment. The "shift-in shift-out" mechanism (SISO), referred to in the applicant's earlier published patents, is to move the beam shaping module (BSM) between a first, treatment position within the gantry and a second non-treatment position removed from the gantry. The SISO mechanism is to facilitate servicing of the beam shaping module. Servicing is achieved by moving the SISO with all of the associated modules into a position where a maintenance engineer can access the modules in an ergonomic way; i.e. to overcome the challenges in accessing components of the device for service. The second main function of the movement mechanism is to reposition the beam shaper and the beam generation module (BGM) after the service tasks have been completed. This is to ensure careful alignment of the beam shaper for treatment. The beam shaper is a complex component of the apparatus and must be readily accessible for maintenance without affecting the accuracy of the treatment.

SUMMARY

However, there are problems associated with the requirement for the SISO mechanism to move one tonne of mass between the service and treatment positions. The present disclosure seeks to help alleviate the potential for the interfacing parts of the SISO mechanism to wear rapidly due to the large mass that is being moved.

In one aspect, the present disclosure provides a moveable support frame for a radiation therapy device, wherein the moveable support frame comprises at least one mass compensation mechanism, wherein the mass compensation mechanism comprises at least one resilient element.

The or each mass compensation mechanism of the present disclosure supports the majority of the forces acting on the moveable support frame when the moveable support frame, or "Shift-in Shift-Out" (SISO) mechanism, is moved between an open/service and a closed/treatment position. This ensures that the interfacing parts between the moveable support frame and the gantry of a radiation therapy device need only provide a locating, positioning function and do not need to support any weight. The moveable support frame of the present disclosure reduces or prevents any possible wear on interfacing parts, such as locating pins and receiving apertures, when the frame is moved between the open/service and closed/treatment positions. The or each mass compensation mechanism minimises the lateral forces on the interfacing parts when the moveable support frame is moved; particularly when it is moved to a closed/treatment position within the gantry of a radiation therapy device. Thus, the present disclosure ensures the accuracy of the isocentre for radiation therapy and also avoids the possibility of the positioning pins being forced into position, which would lead to excessive wear of both the positioning pins and the receiving holes.

Preferably, the or each resilient element has low stiffness.

Preferably, the or each mass compensation mechanism comprises a bending beam; preferably, wherein the bending beam is pre-loaded by at least one resilient element.

Preferably, the or each mass compensation mechanism is held under tension by a pre-tension bolt.

Preferably, the or each mass compensation mechanism further comprises a pre-tension bush.

Preferably, the or each mass compensation mechanism further comprises a rolling means; more preferably, a cam follower.

Preferably, the cam follower is attached to a lever via a cam shaft. More preferably, the lever is attached to the bending beam.

Preferably, the or each rolling means is configured to move the mass compensation mechanism along a ramp.

More preferably, the or each rolling means is configured to move the mass compensation mechanism upwardly along a ramp.

Preferably, the moveable support frame comprises two mass compensation mechanisms.

Preferably, the moveable support frame comprises two mass compensation mechanisms positioned on opposing sides of the moveable support frame.

Preferably, the weight of the moveable support frame and components supported thereon is evenly distributed between two mass compensation mechanisms.

Preferably, the or each mass compensation mechanism is adjustable with respect to the weight of the moveable support frame and/or any components supported thereon.

Preferably, the moveable support frame supports at least one beam generation module.

Preferably, the moveable frame of the movement mechanism supports at least one beam shaping module.

Preferably, the radiation therapy device is an image guided radiation therapy device (IGRT).

In another aspect, the present disclosure provides an image guided radiation therapy (IGRT) apparatus comprising a moveable support frame and/or a movement mechanism as described herein.

BRIEF DESCRIPTION OF DRAWINGS

Within this specification embodiments have been described in a way which enables a clear and concise specification to be written, but it is intended and will be appreciated that embodiments may be variously combined or separated without parting from the disclosure. For example, it will be appreciated that all preferred features described herein are applicable to all aspects of the disclosure described herein and vice versa.

It will be appreciated that reference to "one or more" includes reference to "a plurality".

Figure 1:
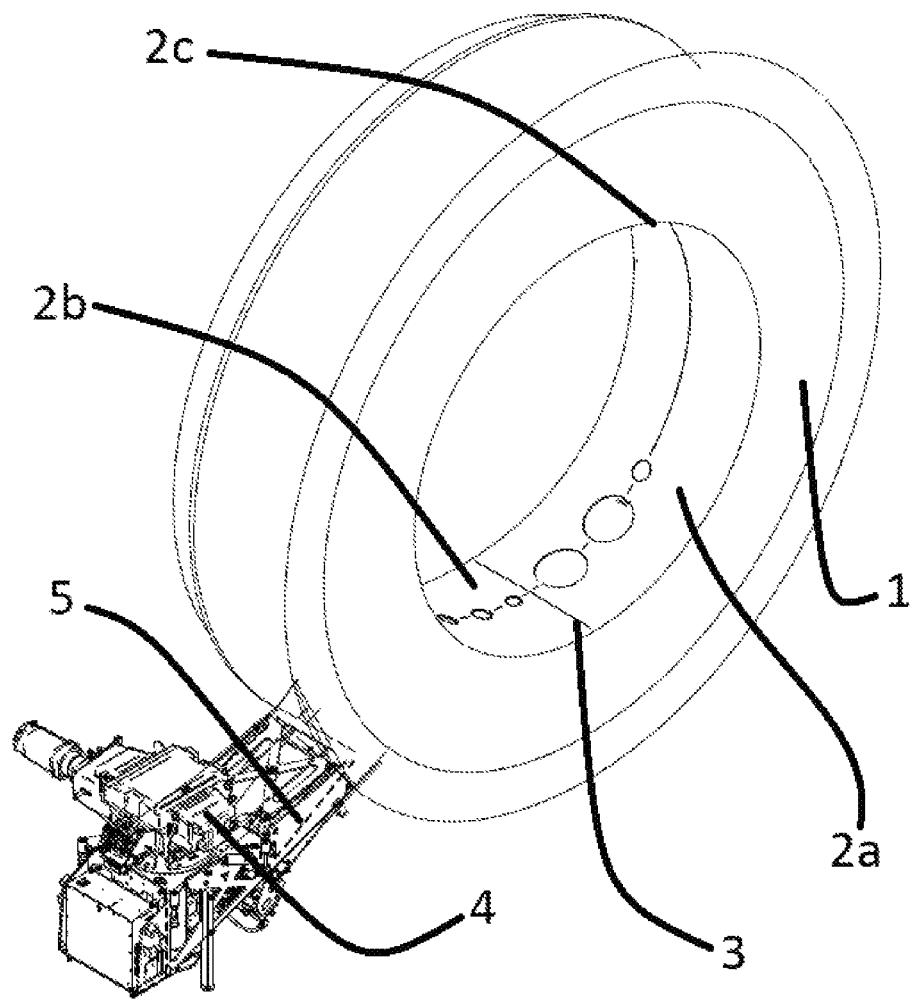
Figure 2:
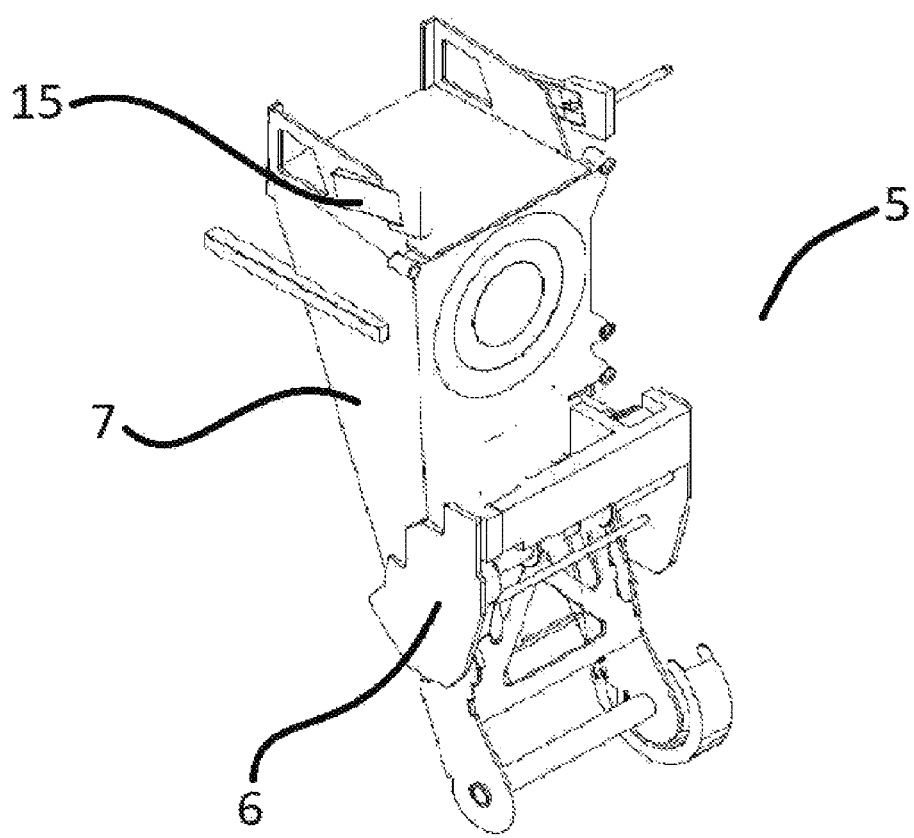
Figure 3:
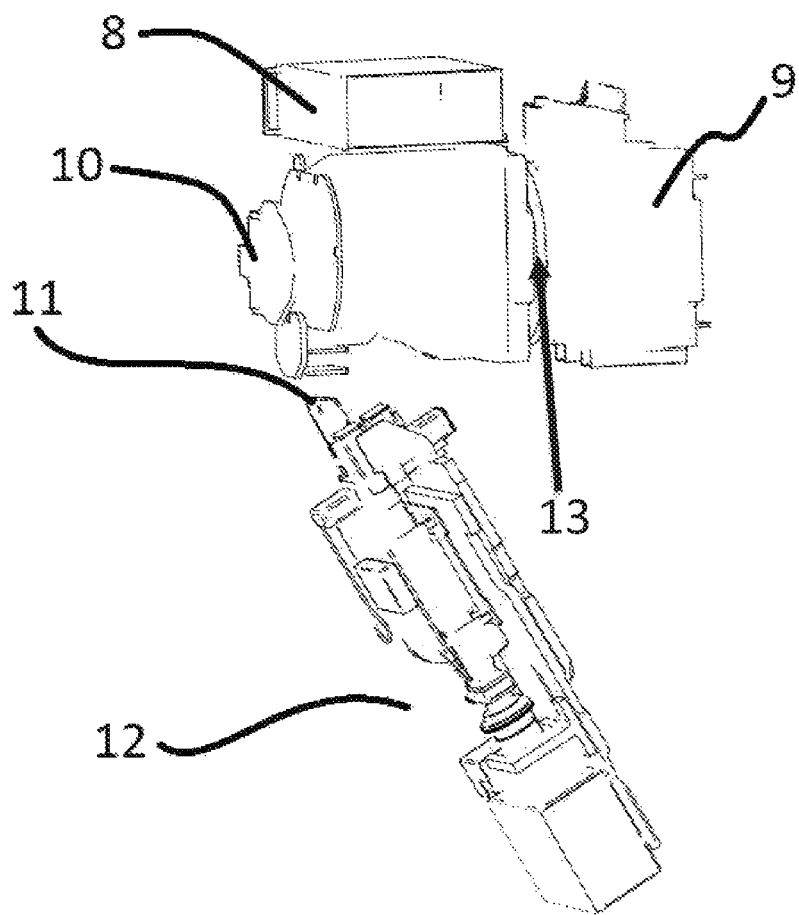
Figure 4:
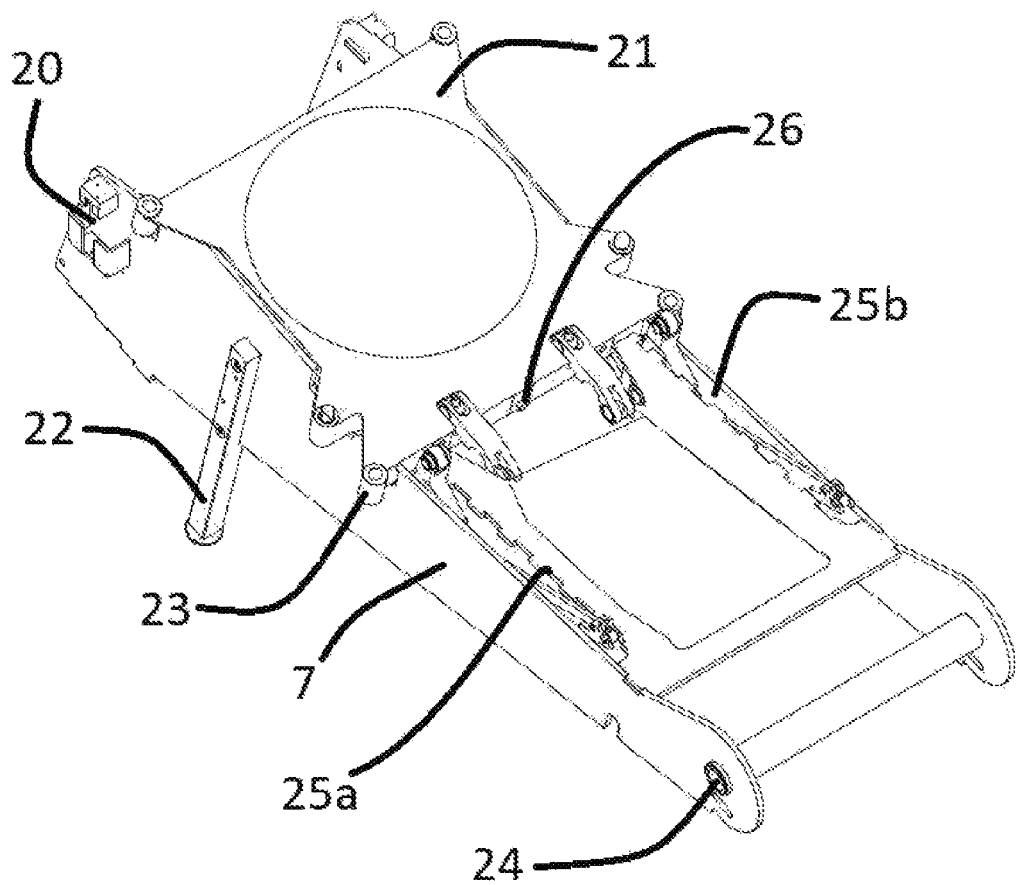
Figure 5:
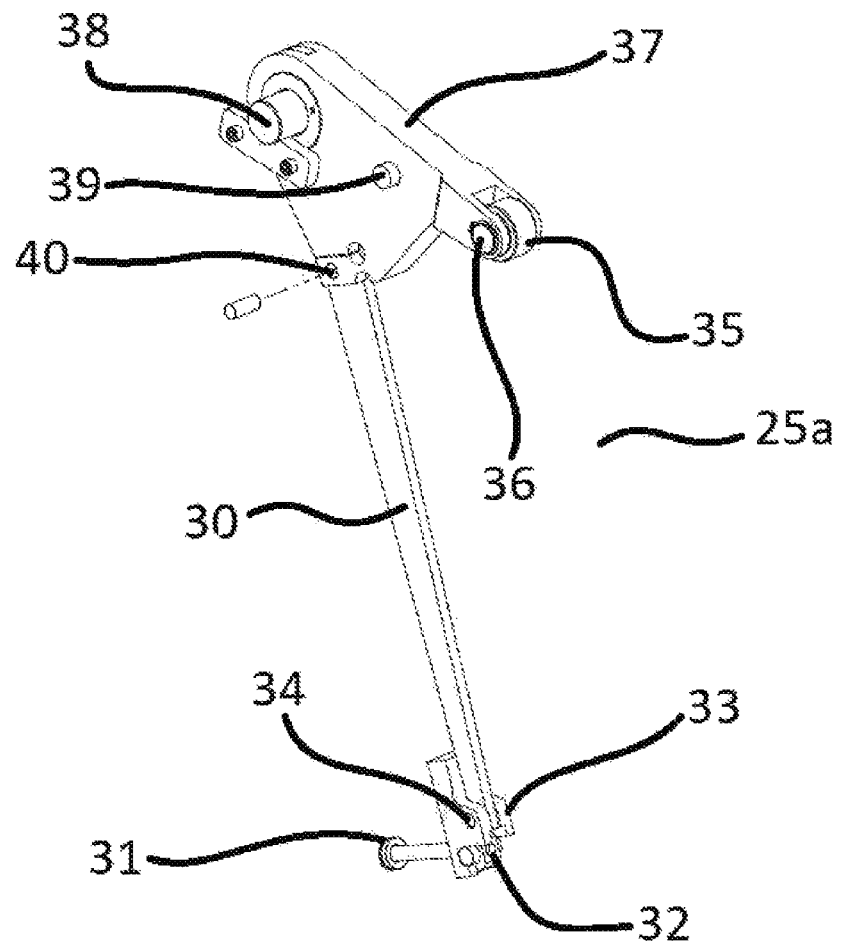
Figure 6A:
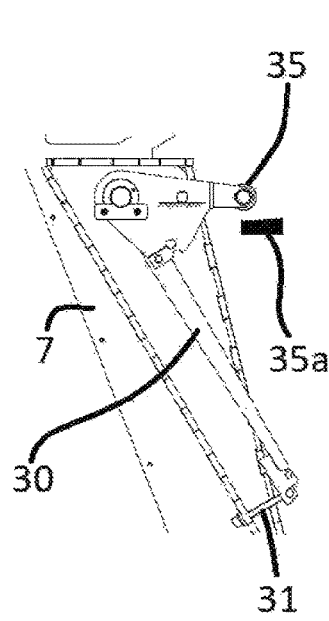
Figure 6B:
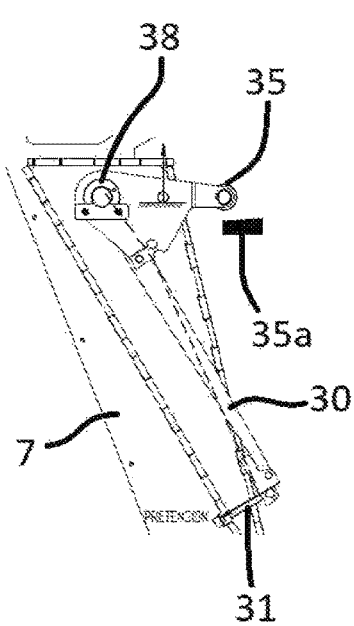
Figure 6C:
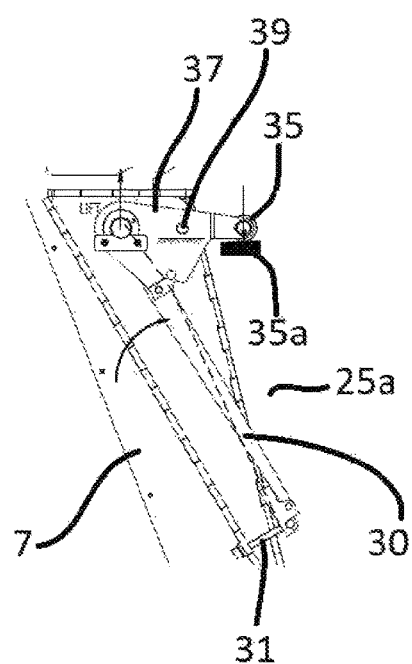

An embodiment of the disclosure will now be described with reference to the accompanying figures in which:

FIG. 1 shows a system overview with a perspective view of a ring gantry of an IGRT apparatus comprising a Shift-In Shift-Out (SISO) mechanism according to the present disclosure and showing the SISO mechanism in an open, non-treatment position for servicing;

FIG. 2 shows a perspective view of the main component parts of the SISO mechanism;

FIG. 3 shows an overview of the beam shaping and beam generation components supported by the SISO mechanism;

FIG. 4 shows a perspective view of the component parts of the SISO moveable support frame;

FIG. 5 shows a perspective view of the component parts of a mass compensation mechanism, in accordance with the present disclosure;

FIGS. 6a, 6b and 6c show a side view of the movement of a mass compensation mechanism for a moveable support frame of an IGRT device in accordance with the present disclosure;

DETAILED DESCRIPTION OF DRAWINGS

FIG. 1 shows a system overview of a dynamic ring gantry 1 of an image guided radiation therapy (IGRT) apparatus. It is understood that the present disclosure is for use with any suitable radiation therapy apparatus and the description of use of the moveable support frame with an IGRT apparatus is by way of example only. The dynamic ring gantry 1 is composed of three arcuate parts 2a, 2b, 2c, which connect together at respective interfaces 3 to form a ring. In use, the radiation therapy apparatus comprises a linear accelerator (LINAC) mounted on the gantry 1 and an MRI scanner (not shown) sits in the aperture of the ring gantry 1 sharing the isocentre. A body to be treated is introduced into a treatment space at the isocentre by means of a sliding table (not shown). The gantry 1 is typically of the order of 2-3 metres in diameter. The IGRT apparatus or other radiation therapy apparatus with which the present disclosure is used, further comprises a beam shaping module 4, such as a multi-leaf collimator (MLC). For treatment to be delivered, a radiation beam emitter module and the beam shaping module 4 are transported around the target by means of the gantry 1.

The beam emitter module and the beam shaping module 4 are moveable between a treatment position within the gantry 1 and a non-treatment position removed from the gantry 1, which is shown in FIG. 1. For servicing of an IGRT apparatus, it is desirable to distance the metal beam shaping module 4 from the very strong magnetic field generated by the MRI components of the IGRT apparatus. The non-treatment/open position, shown in FIG. 1, allows for ease of access to the exposed beam shaping module 4 for servicing, particularly of the MLC. In the non-treatment/service position, the beam shaping module 4 is completely moved outside the gantry 1 so that it is accessible from all sides. The beam shaping module 4 and the beam emitting module of the apparatus are moved by a "Shift-In Shift-Out" (SISO) movement mechanism 5. Movement of the beam shaping module 4 is simultaneous with the movement of the radiation beam emitter components because both of these modules are supported by the SISO 5. This enables the stringent positioning tolerances between these two components to be maintained.

Referring to FIG. 2, the main components of the SISO mechanism 5 are shown, without the beam shaping module 4 and the beam emitting module attached thereto. In use, the SISO movement mechanism 5 holds the beam shaping and beam emitting modules (not shown in FIG. 2) firmly in place. The SISO mechanism 5 comprises a drive assembly 6; a SISO moveable support frame 7 and a SISO safety mechanism 15. The safety mechanism 15 is configured such that, if there is a problem with the movement of the SISO mechanism 5, opening is prevented.

Referring to FIG. 3, the components supported by the SISO moveable support frame 7 are shown separately comprising the beam shaping MLC drive box 8 and the beam shaping collimator head 9. The beam generating components supported by the SISO frame 7 are the beam generation wave guide shielding 10, which is attached by flexible coupling 11 to the beam generation magnetron circulator 12, the beam generation magnetron circulator and the primary collimator, which is not shown on FIG. 3, but its general position is indicated by arrow 13.

Referring to FIGS. 1 and 3, in use, to allow for convenient and effective servicing of the beam shaping components 8, 9, the SISO mechanism 5 moves all beam generation and shaping components 8, 9, 10, 12, 13 from the gantry 1, so that they are easily accessible. When servicing is complete, all beam generation and shaping components 8, 9, 10, 12, 13 are returned to a treatment position within the gantry 1. In a preferred embodiment of the present disclosure, the SISO mechanism 5 is hinged to swivel in and out of the gantry 1.

It is envisaged that the SISO mechanism 5 of the present disclosure fits on any gantry 1 and when the SISO moveable support frame 7 is moved into a closed/treatment position, the pointing accuracy of the treatment beam is restored. Thus, it is envisaged that the SISO interfaces have an accurate position relationship with the X-ray beam optical axis and, on the gantry 1, an accurate position relationship to the gantry isocentre.

In a preferred embodiment of the present disclosure the SISO mechanism 5 is moved between the service/open position and the treatment/closed position using a hoist external to the gantry, or a winch on the gantry. For example, in a preferred embodiment, a winch is positioned below the MLC. The winch lowers and hoists the SISO moveable support frame 7 between the open and closed positions.

Referring to FIG. 4, the components of the SISO frame 7 are shown in more detail. The SISO frame 7 supports the modules that generate and shape the X-ray beam, as described with respect to FIG. 3. In use, the SISO frame 7 moves in and out of the gantry between treatment and service positions, with the forces acting on the SISO frame 7 being highest when the SISO mechanism 5 is opened. In addition to supporting the weight of the beam generation module and beam shaping module 4, the SISO frame 7 also keeps the modules positioned accurately relative to each other. The SISO frame 7 also holds and guides cabling and tubing that form the movement mechanism of the SISO drive assembly 6. The drive assembly 6 comprises a winch and shims that provide an accurate interface between the SISO mechanism 5 and its mounting on the gantry 1. The SISO mechanism 5 further comprises a safety mechanism 15 and a guide mechanism that allows the SISO mechanism to land gently and accurately onto its interfaces with the gantry of the IGRT device.

Referring to FIG. 4, the main components of the SISO frame 7 are shown in more detail comprising two opposing pull-in frame interfaces 20; a SISO interface plate 21; two support legs 22; four locking bolts 23; at least two hinges 24; a left mass compensation mechanism (MCM) 25a and a right mass compensation mechanism (MCM) 25b. The SISO frame 7 also comprises an interface 26 for connection to a winch, which allows the SISO mechanism 5 to be moved between open and closed positions. In use, the primary collimator, wave guide and beam shaping head are mounted on the SISO interface plate 21. Machining accuracy of the SISO interface plate 21 will ensure positioning accuracy between the three components supported thereon (not shown in FIG. 4). On the SISO interface plate 21 the primary collimator interface will be the reference for positioning the SISO assembly 5 onto the gantry 1.

The SISO interface plate 21 is positioned onto the SISO frame 7 by three pins positioned in three V-grooves in the SISO frame 7. The SISO interface plate 21 contains accurate interfaces for positioning the SISO frame 7 on the gantry 1.

With reference to FIG. 5 and FIGS. 6a, 6b and 6c, in order to reduce possible wear on interfacing parts between the SISO mechanism 5 and the gantry 1, during the lifetime of the SISO mechanism 5, the SISO moveable support frame 7 further comprises two opposing mass compensation mechanisms (MCM) 25a, 25b. A left and a right MCM 25a, 25b are each positioned on respective opposing sides of the SISO frame 7.

The component parts of each MCM 25a are shown in FIG. 5. Each MCM 25a comprises a bending beam 30. The bending beam 30 acts as a resilient/spring element and is pre-loaded by a pre-tension bolt 31 and a pre-tension bush 32 at one end of the bending beam 30. The pre-loaded bending beam 30 of each MCM 25a, 25b has relatively low stiffness.

In use, the bending beam 30 of each of the opposing MCMs 25a, 25b is used to suspend the full weight of the SISO mechanism 5, and the components supported thereon, during movement in to and out from the gantry 1. Each pre-loaded bending beam 30, which is pre-tensioned by the pre-tension bolt 31, is adjustable to any weight changes of the SISO mechanism 5; for example, if radiation shielding is added to the beam related modules supported by the SISO moveable support frame 7. Each MCM 25a, 25b supports the weight of the components supported on the SISO frame 7 so that the interfacing components between the SISO frame 7 and the gantry are not supporting weight but serve only to correctly locate the SISO frame 7 when it moves between service and treatment positions.

Referring to FIGS. 6a, 6b and 6c, the resilient element of each MCM 25a, 25b is adjustable according to the pre-loading of the pre-tension bolt 31, so that each MCM 25a, 25b compensates for the exact weight of the SISO frame 7 and components supported thereon. In a further embodiment of the present disclosure, an adjustment tool is provided for adjusting the tensioning of the pre-tension bolt. More tension/pre-loading of the resilient element will increase the height of the SISO frame 7 with respect to the interfacing, positioning pins. Less tension/pre-loading of the resilient element will decrease the height of the SISO frame 7 with respect to the interfacing, positioning pins.

Referring to FIG. 5, an end block 33 adjacent to the pretension bolt 31 further comprises a first dowel pin 34 passing through the bending beam 30. At the opposing end of the bending beam 30, a cam follower 35 having a cam shaft 36 is positioned at one end of a lever 37. The lever 37 is attached to the bending beam 30 via a bearing, shaft and locking plate 38. The lever further comprises an end of stroke (EOS) pin 39 and a second dowel pin 40 passing through the bending beam 30. When the SISO frame 7 is moved to an open/service position the EOS pin 39 will be pressed onto its seating in the SISO frame 7.

Referring to FIG. 5, FIG. 6a, FIG. 6b and FIG. 6c, in use, the cam follower 35 of each MCM 25a, 25b acts as a roller so that, just before insertion of the positioning pins, it will be pulled onto a support ramp 35a (FIG. 6c) so that the SISO frame 7 is lifted to align the locating pins (not shown) with the respective gantry holes (not shown). The support ramp 35a is positioned on the gantry 1. In the embodiment shown, wherein the SISO frame 7 comprises a left and right MCM 25a, 25b, there are two support ramps 35a aligned with the respective cam follower 35 of each MCM 25a, 25b. It has been found that as long as the load of the SISO frame 7 and its components are not supported by the cam follower/roller 35, the EOS pin 39 limits the maximum downward movement of the lever 37 to ensure that the roller 35 is always in the correct position for locating the MCM pins and the gantry holes (not shown).

When the SISO frame 7 is moving to a closed/treatment position within the gantry, the cam follower/roller 35 makes a stroke of about 1 mm relative to the SISO frame 7. This lifts the MCM lever 37 free from the EOS pin 39, such that all force acts on the cam follower 35. In a preferred embodiment of the present disclosure, the MCMs 25a, 25b lift the SISO frame 7 by about 1 mm during closing of the SISO mechanism 5 to a closed/treatment position within the gantry. The MCMs 25a, 25b minimise the lateral forces on the pins whilst allowing for ease of movement in the z-direction; i.e. to allow pin insertion into respective gantry holes and movement of the SISO moveable support frame 7 between open and closed positions.

With reference to FIGS. 6a, 6b and 6c, it has been calculated that the wear of the alignment pins, when calculated for flat on flat surfaces was significantly reduced by use of the mass compensation mechanism 25a, 25b of the present disclosure. It is envisaged that the improvement for a pin-in-hole interface would be even more significant. It was found that the wear height of the pins with the use of the above-described MCMs was around 2.6% of that without the use of the MCMS.

Further embodiments and simple design variations of the embodiments disclosed herein will no doubt occur to the skilled addressee without departing from the true scope of the claims of the disclosure as defined in the appended claims.

The invention claimed is:

1. A moveable support frame for a radiotherapy device, wherein the moveable support frame is a shift-in shift-out mechanism moveable between an open/service position removed from the gantry and a closed/treatment position within the gantry, and comprises at least one mass compensation mechanism, wherein the or each mass compensation mechanism comprises at least one resilient element.

2. A moveable support frame for a radiotherapy device according to claim 1, wherein the or each resilient element has low stiffness.

3. A moveable support frame for a radiotherapy device according claim 1, wherein the or each mass compensation mechanism comprises a bending beam.

4. A moveable support frame for a radiotherapy device according to claim 3, wherein the bending beam is pre-loaded by at least one resilient element.

5. A moveable support frame for a radiotherapy device according to claim 1, wherein the or each mass compensation mechanism is held under tension by a pre-tension bolt.

6. A moveable support frame for a radiotherapy device according to claim 1, wherein the or each mass compensation mechanism further comprises a pre-tension bush.

7. A moveable support frame for a radiotherapy device according to claim 1, wherein the or each mass compensation mechanism further comprises a rolling means.

8. A moveable support frame for a radiotherapy device according to claim 7 further comprising a cam follower.

9. A moveable support frame for a radiotherapy device according to claim 8, wherein the cam follower is attached to a lever via a cam shaft.

10. A moveable support frame for a radiotherapy device according to claim 9, wherein the lever is attached to the bending beam.

11. A moveable support frame for a radiotherapy device according to claim 7, wherein the or each rolling means is configured to move the mass compensation mechanism along a ramp.

12. A moveable support frame for a radiotherapy device according to claim 11, wherein the or each rolling means is configured to move the mass compensation mechanism upwardly along a ramp.

13. A moveable support frame for a radiotherapy device according to claim 1, wherein the moveable support frame comprises two mass compensation mechanisms.

14. A moveable support frame for a radiotherapy device according to claim 13, wherein the moveable support frame comprises two mass compensation mechanisms positioned on opposing sides of the moveable support frame.

15. A moveable support frame for a radiotherapy device according to claim 13, wherein the weight of the moveable support frame and components supported thereon is evenly distributed between two mass compensation mechanisms.

16. A moveable support frame for a radiotherapy device according to claim 1, wherein the or each mass compensation mechanism is adjustable with respect to the weight of the moveable support frame and/or any components supported thereon.

17. A moveable support frame for a radiotherapy device according to claim 1, wherein the moveable support frame supports at least one beam generation module.

18. A moveable support frame for a radiotherapy device according to claim 1, wherein the moveable frame of the movement mechanism supports at least one beam shaping module.

19. A moveable support frame according to claim 1 wherein the radiotherapy device is an image guided radiation therapy device (IGRT).

20. An image guided radiation therapy (IGRT) apparatus comprising a moveable support frame according to claim 1 and a movement mechanism.

* * * * *